US012586451B2

(12) United States Patent
Hatch et al.

(10) Patent No.: US 12,586,451 B2
(45) Date of Patent: *Mar. 24, 2026

(54) HALL MONITOR FOR A HEALTH CARE FACILITY

(71) Applicant: Hatchmed Corporation, Seattle, WA (US)

(72) Inventors: Brian Hatch, Seattle, WA (US); Kyrylo Keydanskyy, Seattle, WA (US)

(73) Assignee: Hatchmed Corporation, Seattle, WA (US)

( * ) Notice: Subject to any disclaimer, the term of this patent is extended or adjusted under 35 U.S.C. 154(b) by 50 days.

This patent is subject to a terminal disclaimer.

(21) Appl. No.: 18/935,274

(22) Filed: Nov. 1, 2024

(65) Prior Publication Data

US 2025/0095459 A1 Mar. 20, 2025

Related U.S. Application Data

(63) Continuation of application No. 18/449,471, filed on Aug. 14, 2023, now Pat. No. 12,165,501, which is a
(Continued)

(51) Int. Cl.
*G08B 5/36* (2006.01)
*G06F 1/26* (2006.01)
(Continued)

(52) U.S. Cl.
CPC .............. *G08B 5/36* (2013.01); *G06F 1/266* (2013.01); *G06F 13/4068* (2013.01); *G07C 9/28* (2020.01); *G16H 40/20* (2018.01)

(58) Field of Classification Search
None
See application file for complete search history.

(56) References Cited

U.S. PATENT DOCUMENTS 3,316,044 A 4/1967 Carbary
3,942,751 A 3/1976 Fay
(Continued)

FOREIGN PATENT DOCUMENTS

CN 201479176 U 5/2010
CN 202949471 U 5/2013
(Continued)

OTHER PUBLICATIONS

"2014 Manufacturers' Excellence Awards Finalists" , Crestron Pyng™ , Accessed from Internet on Jul. 29, 2019 , pp. 1-15.
(Continued)

*Primary Examiner* — Muhammad Adnan
(74) *Attorney, Agent, or Firm* — Kilpatrick Townsend & Stockton LLP

(57) ABSTRACT

A wall-mounted electronic device holder is described. The wall-mounted electronic device holder displays information related to a patient room and/or a patient assigned to the patient room. The wall-mounted electronic device holder includes connections to a hospital communication network and power connections. The wall-mounted electronic devices includes input and output devices, such as a display and configurable light source to project information about the patient and/or the patient room.

20 Claims, 8 Drawing Sheets

Related U.S. Application Data continuation of application No. 17/402,397, filed on Aug. 13, 2021, now Pat. No. 11,727,768.

(60) Provisional application No. 63/065,349, filed on Aug. 13, 2020.

(51) Int. Cl.

| | |
|---|---|
| *G06F 13/40* | (2006.01) |
| *G07C 9/28* | (2020.01) |
| *G16H 40/20* | (2018.01) |

(56) References Cited

U.S. PATENT DOCUMENTS

| | | | |
|---|---|---|---|
| 4,680,790 A | 7/1987 | Packard et al. | |
| 5,273,354 A | 12/1993 | Herrmann et al. | |
| 5,701,991 A | 12/1997 | Helmetsie | |
| 5,802,636 A | 9/1998 | Corbin et al. | |
| 5,822,544 A | 10/1998 | Chaco et al. | |
| 5,867,821 A | 2/1999 | Ballantyne et al. | |
| 6,206,464 B1 | 3/2001 | Santa Rosa et al. | |
| 6,339,410 B1 | 1/2002 | Milner et al. | |
| 6,407,335 B1 | 6/2002 | Franklin-Lees et al. | |
| 6,486,792 B1 | 11/2002 | Moster et al. | |
| 6,622,980 B2 | 9/2003 | Boucher et al. | |
| 7,301,451 B2 | 11/2007 | Hastings | |
| 7,349,203 B2 | 3/2008 | Jobs et al. | |
| 7,458,555 B2 | 12/2008 | Mastropaolo et al. | |
| 7,730,565 B1 | 6/2010 | Masson | |
| 7,778,848 B1 | 8/2010 | Reeves | |
| 7,821,782 B2 | 10/2010 | Doherty et al. | |
| 7,861,985 B2 | 1/2011 | Galvin | |
| 7,967,137 B2 | 6/2011 | Fulbrook et al. | |
| 7,971,289 B2 | 7/2011 | Payne et al. | |
| 7,994,900 B1* | 8/2011 | Langstroth | G16H 40/63 |
| | | | 340/286.07 |
| 8,011,629 B2 | 9/2011 | Herskovic | |
| 8,020,829 B1 | 9/2011 | Tamayori | |
| 8,053,670 B2 | 11/2011 | Lin et al. | |
| 8,461,968 B2 | 6/2013 | Ball et al. | |
| 8,485,404 B2 | 7/2013 | Monaco et al. | |
| 8,499,384 B2 | 8/2013 | Zerhusen | |
| D692,439 S | 10/2013 | Muhlenberg | |
| 8,602,662 B1 | 12/2013 | Mans | |
| 8,607,388 B1 | 12/2013 | Flanagan et al. | |
| 8,650,682 B2 | 2/2014 | Herman | |
| 8,661,583 B2 | 3/2014 | Chinn et al. | |
| 8,727,804 B2 | 5/2014 | McNeely et al. | |
| 8,763,802 B2 | 7/2014 | Ellis-Brown | |
| 8,789,802 B2 | 7/2014 | Springer et al. | |
| 8,794,766 B2 | 8/2014 | Listou | |
| 8,867,198 B2 | 10/2014 | Steele | |
| 8,917,496 B2 | 12/2014 | Richardson et al. | |
| 8,944,826 B1 | 2/2015 | Wilkolaski et al. | |
| 8,972,272 B1 | 3/2015 | Dvorak et al. | |
| 8,994,776 B2 | 3/2015 | Sutherland et al. | |
| 9,038,971 B1 | 5/2015 | Guthrie | |
| 9,147,965 B2 | 9/2015 | Lee | |
| 9,153,112 B1* | 10/2015 | Kiani | G08B 13/22 |
| 9,243,839 B2 | 1/2016 | Kim et al. | |
| 9,286,441 B2 | 3/2016 | Zerhusen et al. | |
| 9,375,374 B2 | 6/2016 | Herman et al. | |
| 9,444,237 B2 | 9/2016 | Frojo | |
| 9,463,126 B2 | 10/2016 | Zerhusen et al. | |
| D773,465 S * | 12/2016 | Palmer | D14/434 |
| 9,573,686 B2 | 2/2017 | Barth | |
| 9,643,767 B2 | 5/2017 | Ziemba | |
| 9,680,518 B2 | 6/2017 | Wojcik et al. | |
| 9,743,357 B2 | 8/2017 | Tabe | |
| 9,824,815 B2 | 11/2017 | Leabman et al. | |
| 10,013,868 B2 | 7/2018 | Cox et al. | |
| 10,028,875 B2 | 7/2018 | Hatch | |
| 10,175,723 B2 | 1/2019 | Weldon | |
| 10,497,472 B1* | 12/2019 | Bullington | H04W 4/029 |
| 10,601,971 B2 | 3/2020 | Hatch et al. | |
| 10,816,937 B2 | 10/2020 | Sidhu et al. | |
| 10,863,012 B2 | 12/2020 | Hatch et al. | |
| 11,096,850 B2 | 8/2021 | Bhimavarapu et al. | |
| 11,132,924 B2 | 9/2021 | Harkness et al. | |
| 11,337,872 B2 | 5/2022 | Bhimavarapu et al. | |
| 11,382,812 B2 | 7/2022 | Bhimavarapu et al. | |
| 11,484,451 B1 | 11/2022 | Nahavandi et al. | |
| 11,727,768 B2 | 8/2023 | Hatch et al. | |
| 11,895,256 B2 | 2/2024 | Hatch et al. | |
| 2001/0022719 A1 | 9/2001 | Armitage et al. | |
| 2004/0174107 A1 | 9/2004 | O'Halloran | |
| 2005/0062380 A1 | 3/2005 | Park et al. | |
| 2005/0071188 A1* | 3/2005 | Thuerk | G16H 40/60 |
| | | | 705/2 |
| 2008/0106374 A1 | 5/2008 | Sharbaugh | |
| 2009/0066486 A1 | 3/2009 | Kiekbusch et al. | |
| 2009/0091458 A1* | 4/2009 | Deutsch | G16H 40/20 |
| | | | 705/2 |
| 2009/0212925 A1 | 8/2009 | Schuman, Sr. et al. | |
| 2009/0255292 A1 | 10/2009 | Benz | |
| 2010/0064721 A1 | 3/2010 | Shin et al. | |
| 2010/0132122 A1 | 6/2010 | Hollingshead | |
| 2010/0324933 A1* | 12/2010 | Giap | G06Q 10/08 |
| | | | 705/30 |
| 2011/0208541 A1* | 8/2011 | Wilson | A61G 7/0527 |
| | | | 705/2 |
| 2011/0210833 A1 | 9/2011 | McNeely et al. | |
| 2011/0214234 A1 | 9/2011 | Herman | |
| 2011/0290807 A1 | 12/2011 | Calvillo et al. | |
| 2012/0026684 A1 | 2/2012 | Matthews | |
| 2012/0092162 A1* | 4/2012 | Rosenberg | G08B 21/245 |
| | | | 340/541 |
| 2012/0153839 A1 | 6/2012 | Farley et al. | |
| 2012/0215360 A1 | 8/2012 | Zerhusen et al. | |
| 2012/0323090 A1 | 12/2012 | Bechtel et al. | |
| 2012/0323591 A1* | 12/2012 | Bechtel | G16H 40/20 |
| | | | 705/2 |
| 2012/0323592 A1* | 12/2012 | Bechtel | G16H 40/20 |
| | | | 705/2 |
| 2013/0093388 A1 | 4/2013 | Partovi | |
| 2013/0253291 A1* | 9/2013 | Dixon | A61B 90/98 |
| | | | 600/323 |
| 2013/0314866 A1 | 11/2013 | Millman | |
| 2014/0188516 A1 | 7/2014 | Kamen et al. | |
| 2015/0024611 A1 | 1/2015 | Wilkolaski et al. | |
| 2015/0277703 A1* | 10/2015 | Davis | G06F 3/04817 |
| | | | 705/2 |
| 2015/0351530 A1 | 12/2015 | Udagawa et al. | |
| 2016/0008197 A1 | 1/2016 | Zerhusen et al. | |
| 2016/0019771 A1* | 1/2016 | Vanderpohl, III | G08B 25/016 |
| | | | 340/679 |
| 2016/0047594 A1 | 2/2016 | Choo et al. | |
| 2016/0128468 A1 | 5/2016 | Lafleche et al. | |
| 2016/0183393 A1 | 6/2016 | Groom et al. | |
| 2016/0190838 A1 | 6/2016 | Webb | |
| 2016/0228091 A1 | 8/2016 | Chiang et al. | |
| 2016/0324701 A1 | 11/2016 | Cambridge et al. | |
| 2017/0035295 A1 | 2/2017 | Collins, Jr. et al. | |
| 2017/0052581 A1 | 2/2017 | Enzinna | |
| 2017/0223482 A1 | 8/2017 | Park et al. | |
| 2018/0168900 A1 | 6/2018 | McNeely et al. | |
| 2018/0225934 A1 | 8/2018 | Moulton et al. | |
| 2018/0247712 A1* | 8/2018 | Muhsin | H01B 11/00 |
| 2019/0259498 A1* | 8/2019 | Sheldon | G06Q 50/22 |
| 2020/0204631 A1* | 6/2020 | Subramaniam | H04L 67/02 |
| 2020/0381094 A1 | 12/2020 | Myers et al. | |
| 2021/0051222 A1 | 2/2021 | Hatch et al. | |
| 2021/0117525 A1 | 4/2021 | Kiani et al. | |
| 2021/0118581 A1* | 4/2021 | Kiani | G06F 21/32 |
| 2022/0051532 A1 | 2/2022 | Hatch et al. | |
| 2022/0066525 A1* | 3/2022 | Hatch | G16H 40/63 |
| 2022/0367043 A1* | 11/2022 | Kayser | G16H 40/63 |

FOREIGN PATENT DOCUMENTS

| | | | |
|---|---|---|---|
| EP | 2575263 A1 | 4/2013 | |
| KR | 20130004443 U | 7/2013 | |

(56)                    References Cited

FOREIGN PATENT DOCUMENTS

| KR | 20170035851 | A  | 3/2017  |
|----|-------------|----|---------|
| WO | 2016155691  | A3 | 12/2016 |
| WO | 2016196403  | A1 | 12/2016 |
| WO | 2017131796  | A1 | 8/2017  |

OTHER PUBLICATIONS

"Announcing New Savant Home Automation Partners: Nest and iPort", INC, Available Online at: https://inctech.net/savant-announces-new-home-automation-partners/ , Sep. 20, 2016 , 2 pages.
"Camera SnakeClamp", SnakeClamp , Dec. 12, 2012 , 3 pages.
"Clamps & Mounts", CTA Digital , Apr. 24, 2016 , 5 pages.
"Iport Or Or Or "Dana Innovations" "Surface Mount with Buttons" or "Launchport with Buttons"", Iport , Accessed from Internet on Jul. 29, 2019 , 2 pages.
"iPort® Announces the Xpress™ Audio Keypad for Sonos®: Direct Wifi Control for Any Sonos Device", Iport , Aug. 30, 2016 , pp. 1-3.
"Medical-Grade Tablet Cases Beat Pathogens", Maximise Technology, Available online at: https://www.maximisetechnology.com.au/medical-grade-device-cases-beat-pathogens-for-health-care/ , 2019 , 4 pages.

"Ram® Torque 3/4™-1" Diameter Handlebar/Rail are with 1", Ball Standard arm and X-Grip® Mounts , Jun. 6, 2016 , 9 pages.
"Rego Patient Interaction System", Curbell Medical , 8 pages.
"Roomie Remote Launches 3.0 App for Home Theater and Home Automation at a Fraction of the Cost of Traditional Touch Panei Systems", Dialog , Sep. 30, 2014 , pp. 1-2.
"Savant Home Automation Works with Nest and iPort, Integrates Deeper with Sonos, PureLink", Available Online at: https://www.cepro.com/news/savant_home_automation_works_with_nest_iport_integrates_deeper_with_sonos/ , Sep. 27, 2016 , 9 pages.
"SVI Trade Awards 2017—The Winners!", SVI , Apr. 27, 2017 , pp. 1-5.
U.S. Appl. No. 15/705,105 , "Non Final Office Action", , 6 pages.
U.S. Appl. No. 15/705,105 , "Notice of Allowance", , 5 pages.
U.S. Appl. No. 16/035,283 , "Notice of Allowance", , 9 pages.
U.S. Appl. No. 16/827,554 , "Non-Final Office Action", , 7 pages.
U.S. Appl. No. 16/827,554 , "Notice of Allowance", , 8 pages.
U.S. Appl. No. 17/087,392 , "Notice of Allowance", , 8 pages.
U.S. Appl. No. 17/402,397 , "Notice of Allowance", , 15 pages.
U.S. Appl. No. 18/449,471 , "Non-Final Office Action", , 9 pages.
U.S. Appl. No. 18/449,471 , "Notice of Allowance", , 9 pages.

* cited by examiner

700

Displaying a first set of information on a display of an electronic device in a surface-mounted electronic device holder. — 702

Receiving authentication information, via an authentication sensor of the surface-mounted electronic device holder. — 704

Displaying a second set of information on the display in response to receiving the authentication information. — 706

HALL MONITOR FOR A HEALTH CARE FACILITY

CROSS-REFERENCE TO RELATED APPLICATION

This application is a continuation of U.S. Non-Provisional application Ser. No. 18/449,471, filed Aug. 14, 2023 which is a continuation of U.S. Non-Provisional application Ser. No. 17/402,397, filed Aug. 13, 2021, which was granted on Aug. 15, 2023 as U.S. Pat. No. 11,727,768, which claims the benefit of and priority to U.S. Provisional Application No. 63/065,349, filed Aug. 13, 2020, and titled "HALL MONITOR FOR A HEALTH CARE FACILITY," the content of which is herein incorporated by reference in its entirety for all purposes.

BACKGROUND OF THE INVENTION

Portable electronic devices (PEDs) (e.g., digital tablets, smart phones, and other electronic devices) are becoming more popular and prevalent in modern day lifestyles. Hospitals are experiencing increased usage of PEDs, either by patients and/or by hospital personnel. PEDs are being used in hospitals for communication, education, video conferencing with a patient who is in a hospital bed, and entertainment of the patient.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments herein are directed to portable electronic device (PED) related assemblies that are employable in a health care facility and can support the use of a PED or other electronic device on a wall of the health care facility to provide access to data and receive inputs and/or signals from users. In some embodiments, a PED related assembly includes one or more communication, data, and/or power cable assemblies that can be readily disconnected interchange, remove, or otherwise interact with the device. In some embodiments, a PED related assembly includes a PED holder with an output connector that is connectable to an input port of a PED held in the PED holder. As a result, a PED can be supplied power and/or data via a connection that enables use of the PED.

One general aspect includes a surface-mounted electronic device holder including a housing to contain an electronic device including a display, the housing including a first portion adapted for mounting the surface-mounted electronic device holder to a surface of a health care facility, the housing also including a second portion defining an opening through which the display is accessible by a user. The holder also includes one or more interfaces adapted for connection to at least one of a power or a data cable of a health care facility, the one or more interfaces disposed in the housing, where: a first interface of the one or more interfaces is operatively coupleable with the electronic device such that power received from the power and data cable is provided from the first interface to the electronic device, and a second interface of one of the one or more interfaces is operatively coupled with a communication system of the health care facility such that a signal is provided from the second interface to the communication system via the power and data cable.

One general aspect includes a surface-mounted electronic device holder for placement outside of a patient room. The surface-mounted electronic device holder also includes an electronic device including a processor, memory, and visual interface. The holder also includes a housing enclosing a space to contain the electronic device; a first interface operatively coupleable with the electronic device such that power received from a power over ethernet (poe) cable is provided from the first interface to the electronic device, and one or more configurable light emitting devices positioned on the housing.

One general aspect includes a method. The method also includes placing a housing of a surface-mounted electronic device holder on a surface adjacent a patient room of a health care facility. The method also includes placing an electronic device within the housing. The method also includes connecting the electronic device to a power and data cable, the power and data cable operably coupling the electronic device to one or more systems of a health care facility. The method also includes connecting the electronic device to a light emitting device connected to the housing. The method also includes securing the electronic device within the housing.

One general aspect includes a method. The method also includes displaying, on a display of an electronic device positioned in a surface-mounted electronic device holder associated with a patient room, a first set of information including data corresponding to a status of the patient room. The method also includes receiving authentication information, via an authentication sensor, associated with an individual located in proximity to the electronic device positioned in the surface-mounted electronic device holder. The method also includes displaying, on the display, a second set of information in response to receiving the authentication information, the second set of information including data corresponding to a patient within the patient room.

BRIEF DESCRIPTION OF THE DRAWINGS

The specification makes reference to the following appended figures, in which use of like reference numerals in different figures is intended to illustrate like or analogous components.

DETAILED DESCRIPTION

In the following description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Some embodiments herein are directed to a surface-mounted (e.g., wall-mounted) electronic device holder positioned on a wall outside a room of a health care facility. The surface-mounted electronic device holder may include information such as an identifier of the room as well as information related to the health care facility. The electronic device contained within the holder may be a self-contained electronic device, such as a personal electronic device (PED), or may be a built-in electronic device. The electronic device may be connected to a wired or wireless network of the health care facility and may also be connected to one or more other electronic devices through a wireless or wired connection, such as through an Ethernet cable which may provide both power and data connections to the electronic device, for example through a power-over-Ethernet (POE) connections.

In some examples, the wall-mounted electronic device holder may be positioned within the room, or may be positioned away from the room, such as at a standalone station where personnel may interact with the electronic device, such as to update health records of patients within the facility.

The wall-mounted electronic device holder may also include additional means of displaying information, such as with moveable flags to attract attention, projected displays, illuminated lights, sound-producing devices, and other such output devices.

In some examples, the wall-mounted electronic device holder may provide a voice and/or a video communication interface into a room of the healthcare facility, for example for a physician to check on the status of a patient before entering a room. The device holder may include input devices, such as a physical button to interact with the electronic device, a microphone, touch screen, and other such input devices for interacting with the electronic device in various ways.

Figure 1:
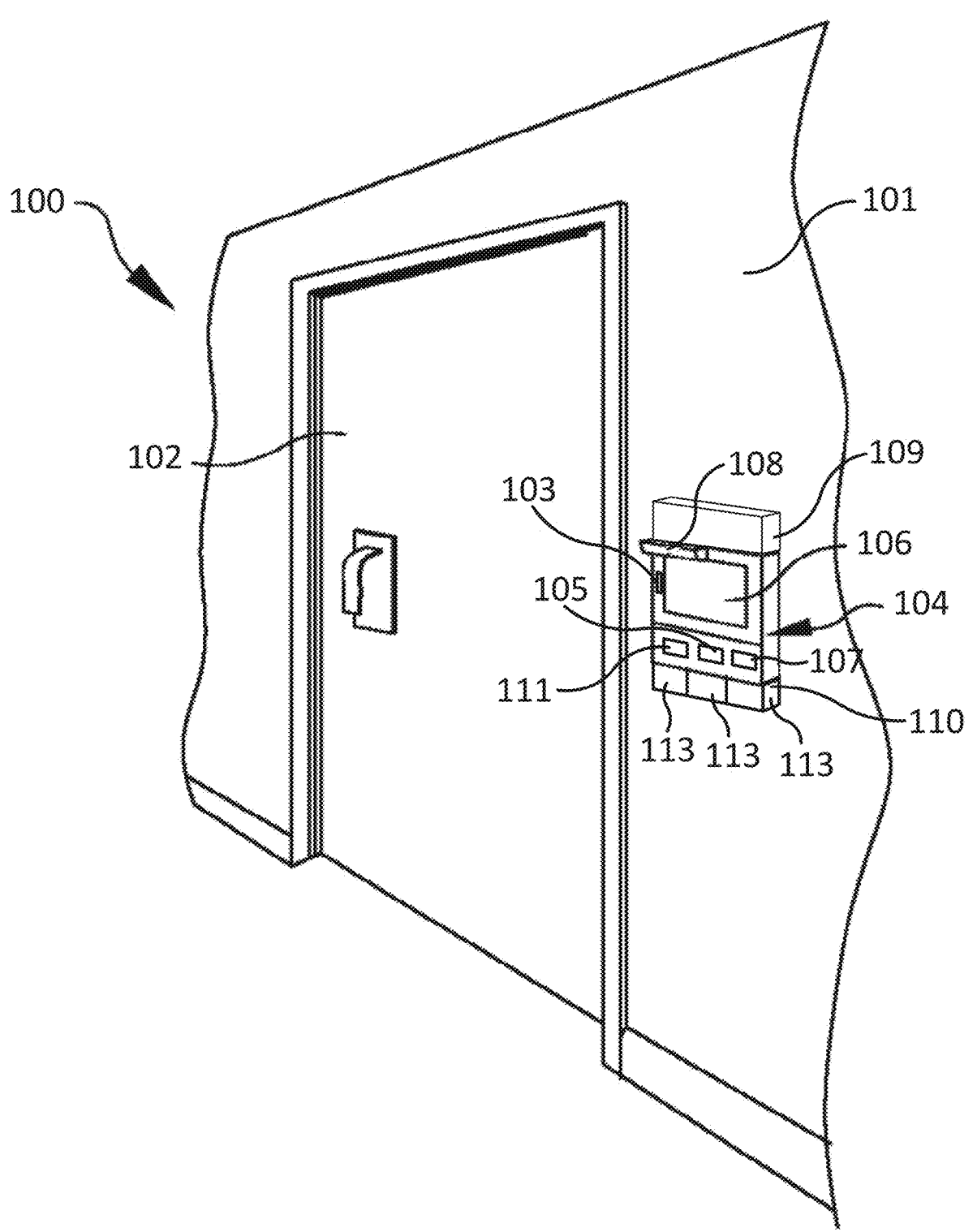
FIG. 1 shows a doorway in a hospital facility with a PED holder assembly positioned on the wall to present information and receive inputs, in accordance with some embodiments.

Turning now to the drawing figures in which the same or similar reference identifiers refer to the same or similar components throughout all of the drawing figures, FIG. 1 shows the entrance to a patient room 100 with a surface-mounted electronic device holder 104 positioned on a wall 101 of a health care facility adjacent a door 102. The surface-mounted electronic device holder 104 may include one or more displays 106. In various embodiments, the displays 106 may be or include a PED as described herein.

However, the displays 106 may be separate from a PED. For example, the displays 106 may be or include a monitor that can display data, for example, data received from a PED.

The surface-mounted electronic device holder 104 may also include physical identification information, such as a marking indicating a room such as a room number in alphanumeric characters and/or other characters such as braille or other fixed features on a housing 110. For example, the surface-mounted electronic device holder 104 can include a plate 111 that can include the markings (e.g., a room number, notes, and/or braille). The plate 111 can be or include a removable plate. For example, the plate 111 can be removed and replaced with a different plate 111. In some embodiments, the plate 111 can include a surface on which notes may be written directly (e.g., a surface that is non-permeable and smooth capable of writing on with dry-erase markers, whiteboard markers, and the like). The housing 110 may additionally or alternatively include devices 108 for attaching or affixing temporary placards, papers, notes, and other such materials that may be placed or referenced by staff within the healthcare facility. The housing 110 may include a surface on which notes may be written directly, such as a surface that is non-permeable and smooth capable of writing on with dry-erase markers, whiteboard markers, and the like. In some embodiments, the housing 110 can be attached to the wall 101 via a pivoting mount. The pivoting mount can allow the housing 110 to pivot relative to the wall 101. For example, the pivoting mount can allow the housing 110 to tilt up or down and/or side to side.

The housing 110 can include one or more pieces. For example, the housing 110 can be or include multiple pieces that can be connected to form an interior volume. However, the housing 110 may be a single piece. For example, the housing 110 can be a single piece with an opening for inserting, for example, a PED. In some embodiments, the housing 110 can include a panel and/or a door. The panel and/or the door can be concealed on the housing 110. The panel and/or the door can include slides, hinges, or any suitable movement component.

In various embodiments, the housing 110 can include a holder 105. The holder 105 can hold various objects. For example, the holder 105 can be or include a hook for holding, for example, keys. The holder 105 can additionally or alternatively be or include a holder for a stylus.

In further embodiments, the housing 110 can include one or more buttons 107. The buttons 107 can be used, for example, to control the PED and/or the display 106. For example, the buttons 107 can be or include volume control buttons. The buttons 107 can additionally or alternatively be used to control a TV (e.g., a TV in the patients room) and/or a climate control system (e.g., a climate control system in the patients room). The buttons 107 can additionally or alternatively be or include a panic button. The panic button can be connected with the speaker 134 discussed in reference to FIG. 5. The buttons 107 can additionally or alternatively be or include a call button and/or a service button. For example, the buttons 107 can call a doctor and/or a nurse, for example, to the patients room 100.

In various embodiments, the surface-mounted electronic device holder 104 can include a disinfecting unit 109. The disinfecting unit 109 can be attached to the housing 110 and positioned to disinfect the housing 110, the displays 106, and/or any suitable surface of the surface-mounted electronic device holder 104. For example, the disinfecting unit 109 can be positioned on the top of the housing 110 and oriented downward to disinfect the front face of the surface-mounted electronic device holder 104. The disinfecting unit

109 can continuously and/or periodically disinfect the front face of the surface-mounted electronic device holder 104. For example, the disinfecting unit 109 can disinfect the surface-mounted electronic device holder 104 after an individual has interacted with the surface-mounted electronic device holder 104. However, the dispensing unit 109 may disinfect the surface-mounted electronic device holder 104 at timed intervals or may continuously disinfect the surface-mounted electronic device holder 104. The disinfecting unit 109 can be or include an ultraviolet light, a disinfecting light, a disinfectant dispenser, and/or any suitable device for emitting or dispensing a disinfecting light and/or a disinfecting solution. Additionally or alternatively, multiple disinfecting units 109 can be included in the surface-mounted electronic device holder 104. In this case, a disinfecting unit 109 can be used to disinfect components that do not belong to the electronic device holder 104. For example, this disinfecting unit 109 can include a slot for inserting a card, a mobile device, a hand, etc. and the inserted component is treated (e.g., with UV light and/or a disinfecting or antimicrobial solution). This disinfecting unit 109 can also be a soap dispenser.

In further embodiments, the surface-mounted electronic device holder 104 can include one or more slots 113. The slots 113 can have an interior volume and one or more components for interacting with an item that may be positioned within the interior volume. For example, a slot 113 can include an interior volume for receiving a cell phone and include a charge port, a charging surface (e.g., for wireless device charging), and/or a charging cable which can be used to charge the cell phone inserted into the slot 113. In further embodiments, the slot 113 can include an ultraviolet (UV) light and/or a similar disinfecting light that can disinfect an item (e.g., a phone) inserted into the interior volume of the slot 113. The slots 113 can additionally or alternatively be or include a dispenser, for example, dispensers for dispensing disinfecting solution. For example, the slots 113 can be or include a dispenser for dispensing disinfecting soap and/or hand sanitizer.

In various embodiments, the surface-mounted electronic device holder 104 can include an authentication sensor 103. For example, the authentication sensor 103 can detect a user and send instructions to unlock the displays 106 and/or the PED. The authentication sensor 103 can be or include a biometric authentication sensor.

Figure 2:
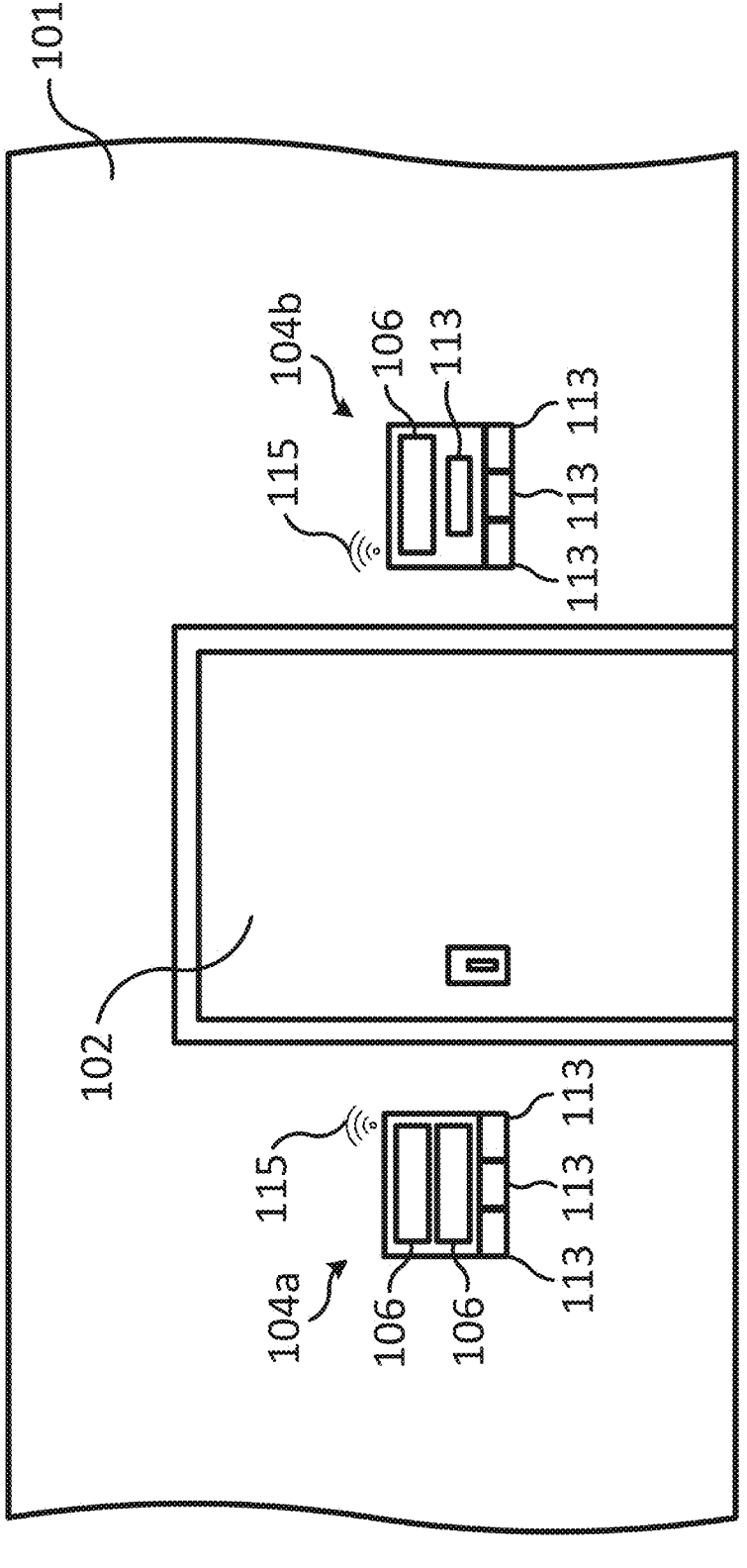
FIG. 2 shows a doorway in a hospital facility with multiple PED surface-mounted PED holder assemblies positioned on a wall to present information and receive in puts, in accordance with some embodiments.

Turning now to FIG. 2, the entrance to the patient room 100 is shown with surface-mounted electronic device holders 104 positioned on the wall 101 on opposing sides of the door 102. The surface-mounted electronic device holders 104 can be the same type (e.g., can have the same components and/or interfaces), however, the surface-mounted electronic device holders 104 may be different types (e.g., have different components and/or interfaces). For example, the surface-mounted electronic device holder 104a can include multiple displays 106 and the surface-mounted electronic device holder 104b can include a display 106 and a plate 111. The surface-mounted electronic device holders 104 can include communication hardware 115. The communication hardware 115 can communicate with other surface-mounted electronic device holders 104, the PED, and/or other components in the patent room 100 and/or hospital. For example, the communication hardware 115 can communicate with lights in the patient room 100 (including surgical lights and/or IoT or non-IoT specialty commercial lighting), a sound system in the patient room 100, a nurse call system, another surface-mounted electronic device holder (to form an mesh network using a communication protocol, such as BLUETOOTH®), and/or similar components. Further, a surface-mounted electronic device holder (e.g., 104a and/or 104b) can include RTLS hardware (e.g., a radio frequency (RF) tag or RTLS repeater) to enable real-time locating systems (RTLS) determination of the location of the surface-mounted electronic device holder (e.g., as described herein, such a holder can be released from a wall and moved around). Additionally or alternatively, the RTLS hardware can enable the locating of other components (e.g., mobile devices or nurse devices) by using one or more RTLS techniques (e.g., by receiving signals from RTLS tags included in such components). In this way, the surface-mounted electronic device holder can determine in real-time the locations of such components.

Figure 3:
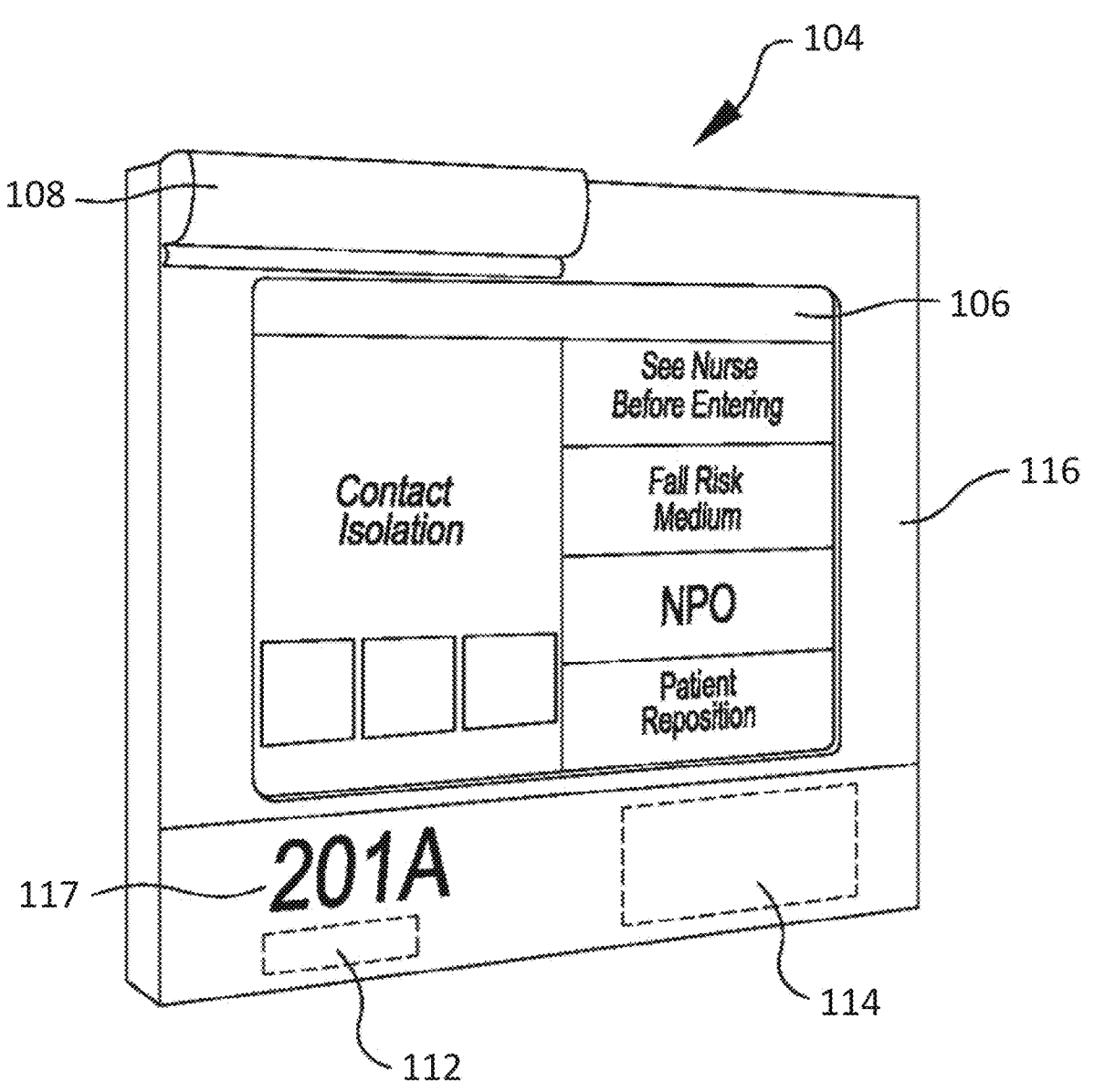
FIG. 3 shows a surface-mounted PED holder assembly including a display of the PED and device for receiving input data, in accordance with some embodiments.

Turning now to FIG. 3, a surface-mounted electronic device holder 104 (hereafter "holder 104") is shown with enclosing an electronic device including a display 106. The housing 116 defines an opening around the display 106 where the display 106 is visible and a user may interact with the display 106. The surface-mounted electronic device holder 104 may also include additional means of displaying information, such as with moveable flags to attract attention, projected displays, illuminated lights, sound-producing devices, and other such output devices. The surface-mounted electronic device holder 104 includes room identifying information 117 as well as the electronic device displaying information about the room, patient, or other such information. The surface-mounted electronic device holder 104 may also include input and output devices as described above. The surface-mounted electronic device holder 104 may also include connections for data and power connection of the electronic device to a system of the health care facility. The holder may also include proximity sensors 112, and authentication devices 114, where the proximity sensors 112 and/or the authentication devices 114 may include RFID sensors, Near Field Communication (NFC) devices, Bluetooth devices, and/or other such sensors for, as applicable, detecting a presence of and/or receiving authentication information for verifying an identity of an individual who approaches the room. Additional features of the surface-mounted electronic device holder 104 may include physical buttons for interacting with the electronic device, vent holes, securing features such as security screws, sliding locks, magnetic locks, and the like to prevent removal of the electronic device, except by authorized personnel.

In some examples, the surface-mounted electronic device holder 104 may be releasably secured to the wall, or other surface, through the use of a releasable securement or locking device. The releasable securement may include a slider, hook, magnetic latch, or other such releasable attachment mechanism. The releasable securement may enable the surface-mounted electronic device holder 104 to be carried into a patient room or within some limited predetermined range, such as set by beacons, geofences, or other such limitations. Upon passing or reaching such geographic limitations a signal may be conveyed to generate a notification that the holder 104 has been removed to a system of a healthcare facility. Additionally warning signals and/or tracking information may be included to aid in recovery of the device if removed.

In some examples, the surface-mounted electronic device holder 104 may be released, such that the surface-mounted electronic device holder 104 is removable from the wall, or other surface, after an identity of a user has been authenticated, for example using the authentication device 114 described herein. For example, a caregiver may approach the surface-mounted electronic device holder 104, adjacent a patient room, and may authenticate their identity with appropriate credentials, upon authentication of credentials the releasable securement may enable removal of the surface-mounted electronic device holder 104, or a portion of the surface-mounted electronic device holder 104 from the wall such that the caregiver can carry the surface-mounted electronic device holder 104 with the electronic device into the patient room for use in taking notes or otherwise facilitating caregiving tasks. The releasable securement may receive a signal from the electronic device, or a controller device, in response to verification of the authentication credentials, the signal releasing a mechanical, electrical, magnetic, or other actuatable locking mechanism such that the surface-mounted electronic device holder 104 may be removed. Before authentication of the caregiver, the surface-mounted electronic device holder 104 may be locked in place and not removable.

The display 106 may include information related to care of the individual in the room, reservation, order, or other such information, and may include information gathered from within the room, including information relating to a position of the bed, an alert light signaled by an alert switch, or other such information.

Figure 4:
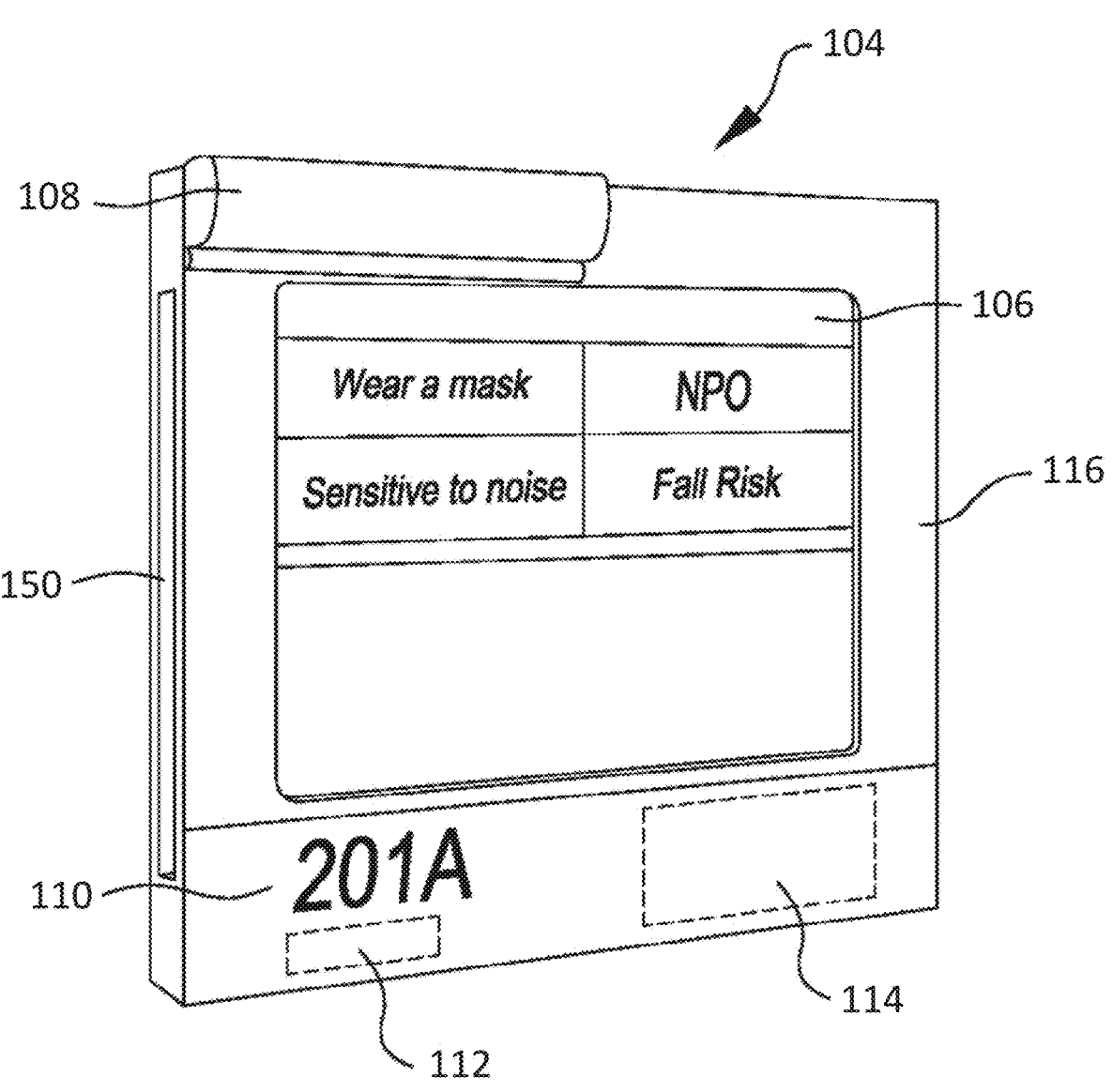
FIG. 4 shows a surface-mounted PED holder assembly including configurable illumination devices around the perimeter of the assembly, in accordance with some embodiments.

Turning now to FIG. 4, the surface-mounted electronic device holder 104 is shown including configurable light emitting devices 370 around the perimeter of the housing 116. The light emitting devices 370 may provide a visual indication of a room status, for example with green lights or dim lights indicating a normal condition while flashing lights or red lights may indicate an emergency status within the room. The light emitting devices 370 may also indicate, for example that the patient is resting, reclined, out of the room, or any other patient status. In some examples, the light emitting devices 370 may be accompanied by or replaced with one or more projection devices to project displays onto a floor, ceiling, or wall of the health care facility. The projection may indicate, for example a stop sign to indicate that a room should not be entered, or to project some particular information relating to a patient. The light emitting devices 370 may be configured based upon a signal from the electronic device or based on a signal from a central system of the health care facility.

In some examples, the surface-mounted electronic device holder 104 may be accompanied by one or more peripheral devices, such as a hand sanitizing station. The electronic device may be linked to the station such that confirmation of personnel sanitizing hands can be accomplished. This may include a proximity sensor, camera, contact sensor, or other such means of confirming use of the hand sanitizing station. In some examples, the person may approach a room and the illumination panels may illuminate in a first color, red. The electronic device may display a message instructing the person to sanitize their hands. Following confirmation of hand sanitizing, the lights may change to green, indicating the person may enter the room.

In some examples, the surface-mounted electronic device holder 104 may include sensors to receive proximity information and/or identifying information, such as RFID sensors, Near Field Communication (NFC) devices, and/or Bluetooth devices acting as authentication devices 114. The electronic device, or a system of the health care facility, may determine proximity and/or verify the identity of the person and perform an action. For example, the lights of the holder may indicate that a person should not enter a room, or that a room is secured. Following verification of the identity of the person, the lights may change color to indicate the person may enter the room. In some examples a lock or other such system may also be controlled such that only authorized persons can enter a room of the health care facility. In some examples, the electronic device may display a first set of information and subsequently, after verification of an identity of an individual, may display a second set of information as described with respect to FIG. 7. For example, the display may initially present general information and, upon verification of the identity of a health care professional, may display patient information to the professional for their use. Such personal information is thereby protected for the patient and easily accessible to the professional. In some examples, the surface-mounted electronic device holder may include one or more interfaces for communicating with other electronic devices, such as through BLUETOOTH®. The other electronic devices may include electronic devices of personnel associated with the health care facility, for example to update patient records from a physician device.

Figure 5:
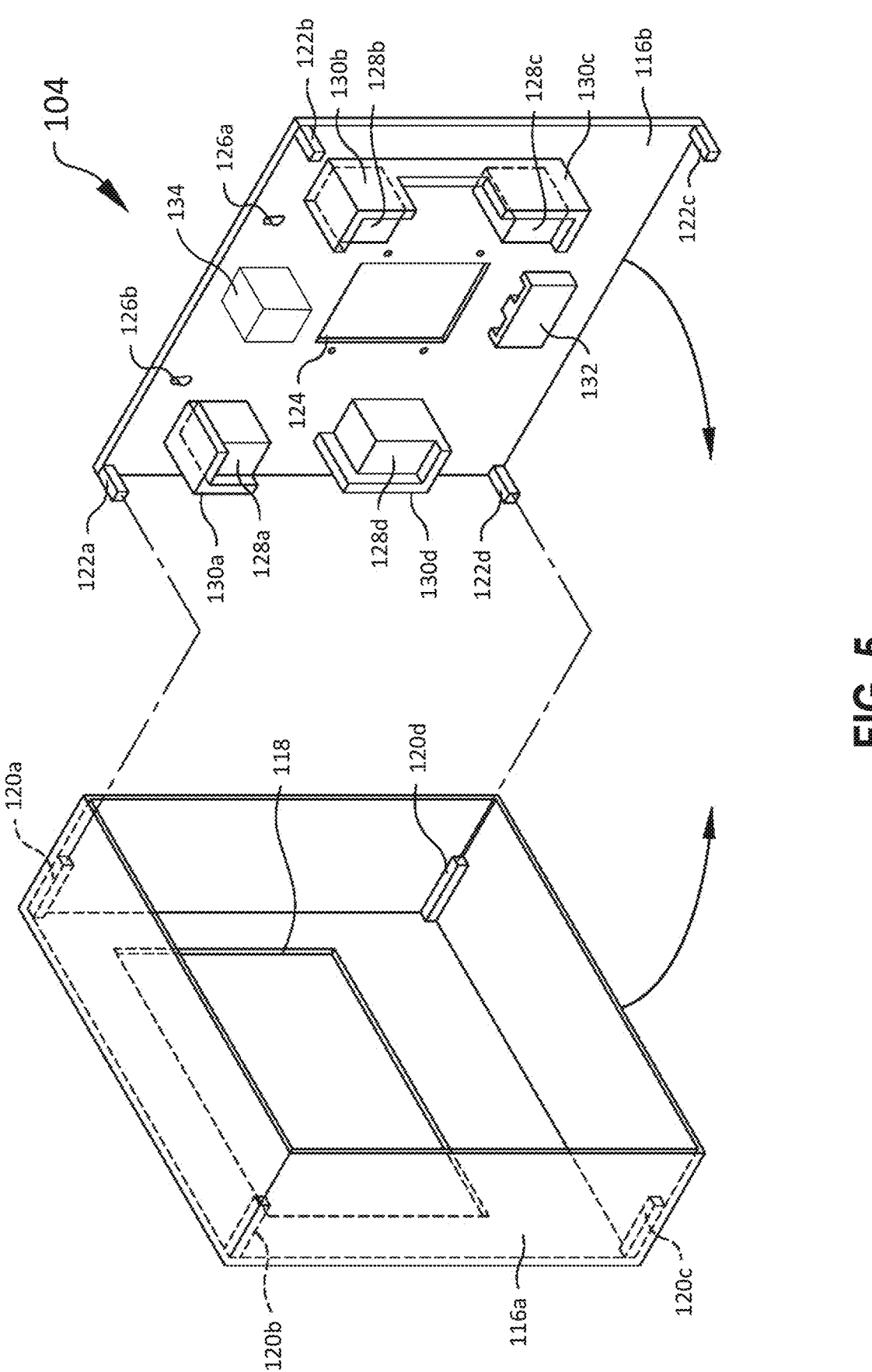
FIG. 5 shows the surface-mounted PED holder assembly in an open configuration, in accordance with some embodiments.

Turning now to FIG. 5, the surface-mounted electronic device holder 104 is shown in an open configuration, in accordance with some embodiments. As illustrated, the surface-mounted electronic device holder 104 may be formed of two or more components, such as a front 116A and a back 116B. In some examples, the surface-mounted electronic device holder 104 may be a unibody assembly with an opening to insert or access an electronic device contained therein. The front 116A defines an opening 118 through which a display of the electronic device may be visible and/or interacted with. For example, the display may include a touchscreen that can be interacted with by a user through opening 118. The touchscreen can be a negative pressure control screen to control operations available at the surface-mounted electronic device holder 104. Additionally or alternatively, a negative pressure control screen can be used for such controls.

In various embodiments, the opening 118 can be or include a bezel. The bezel can be adjustable, for example, based on the size of the display 106 and/or the PED. For example, the opening 118 can be adjusted (e.g., made larger or smaller) depending on the size of the display 106 and/or the PED.

The front 116A includes walls and also includes internal components 120 for interfacing with components of back 116B to positively engage when assembled together. The internal components 120 are shown as blocks that rest in the corners of the front 116A such that when front 116A and back 116B are assembled together internal components 122 on the back 116B engage with the corners of the front 116A as well as the internal components 120 so positively engage and secure the front 116A and back 116B together in a single location and orientation. Additional features, including security screws, magnets, cam-locks, pins, or any other such fasteners may be used to secure the front 116A and the back 116B together.

The back 116B defines an opening 124 where one or more connections or interfaces 312 may be inserted to connect an electronic device within the surface-mounted electronic device holder 104 to other systems, such as systems and networks of a hospital, including power and data connections, such as a POE connection as described herein. The POE connection may provide a power and data connection to enable the exchange of information as well as power to the electronic device without the need for more than a single interface or cable. In some examples, the surface-mounted electronic device holder 104 may also enclose a backup power supply, such as a battery backup that enables the electronic device or peripherals attached thereto (cameras, lights, sensors) to continue to function independent of a wired power connection. Connections to power and data, such as through POE connections are included within the holder and provide a conduit for communication between the electronic device and a system of the health care facility.

The electronic device within the surface-mounted electronic device holder 104 may communicate with other devices, such as other hospital equipment, for example to display information related to a status of various devices and/or equipment in a patient room. The electronic device may be entirely standalone, not requiring computing power or resources of a remote computing device or server. In some examples, the electronic device may communicate with one or more elements within the surface-mounted electronic device holders 104, or within an environment entirely over BLUETOOTH®.

In various embodiments, the surface-mounted electronic device holder 104 can include cradling features 130 positioned within the housing 110. The cradling features 130 can support an electronic device, a display of an electronic device, or the one or more displays 106, for example, to maintain the electronic device and/or the displays 106 such that the display 106 and/or the display of the electronic device is aligned with the opening 118. The cradling features 130 can be or include posts, magnets, suction cups, hook and loop fasteners, fasteners, adhesives, one or more ledges, one or more indentations in the housing 110, and/or any suitable feature or device that can support the electronic device to align the display of the electronic device with the opening 118.

In various embodiments, the cradling features 130 can include rear surfaces 128 to support a back of the electronic device and also include raised edges to resist and/or prevent lateral and/or vertical movement of the electronic device. Though illustrated with four cradling features 130, in some embodiments more or less cradling features 130 may be included to support the electronic device in the surface-mounted electronic device holder 104. In some embodiments, the cradling features 130 may be moveable to support electronic devices of different sizes.

In various embodiments, the surface-mounted electronic device holder 104 can include one or more speakers 134, for example, at least partially positioned within the housing 110. The speakers 134 can communicate with the PEDs and/or the displays 106 to communicate with a patient and/or hospital staff. For example, the speakers 134 can be used to communicate alarms. The speakers 134 can additionally or alternatively be used to communicate with the speakers 134 in other PEDs and/or displays 106. For example, the speakers 134 can be used as part of a communication device for communicating with other PEDs and/or displays 106.

Figure 6:
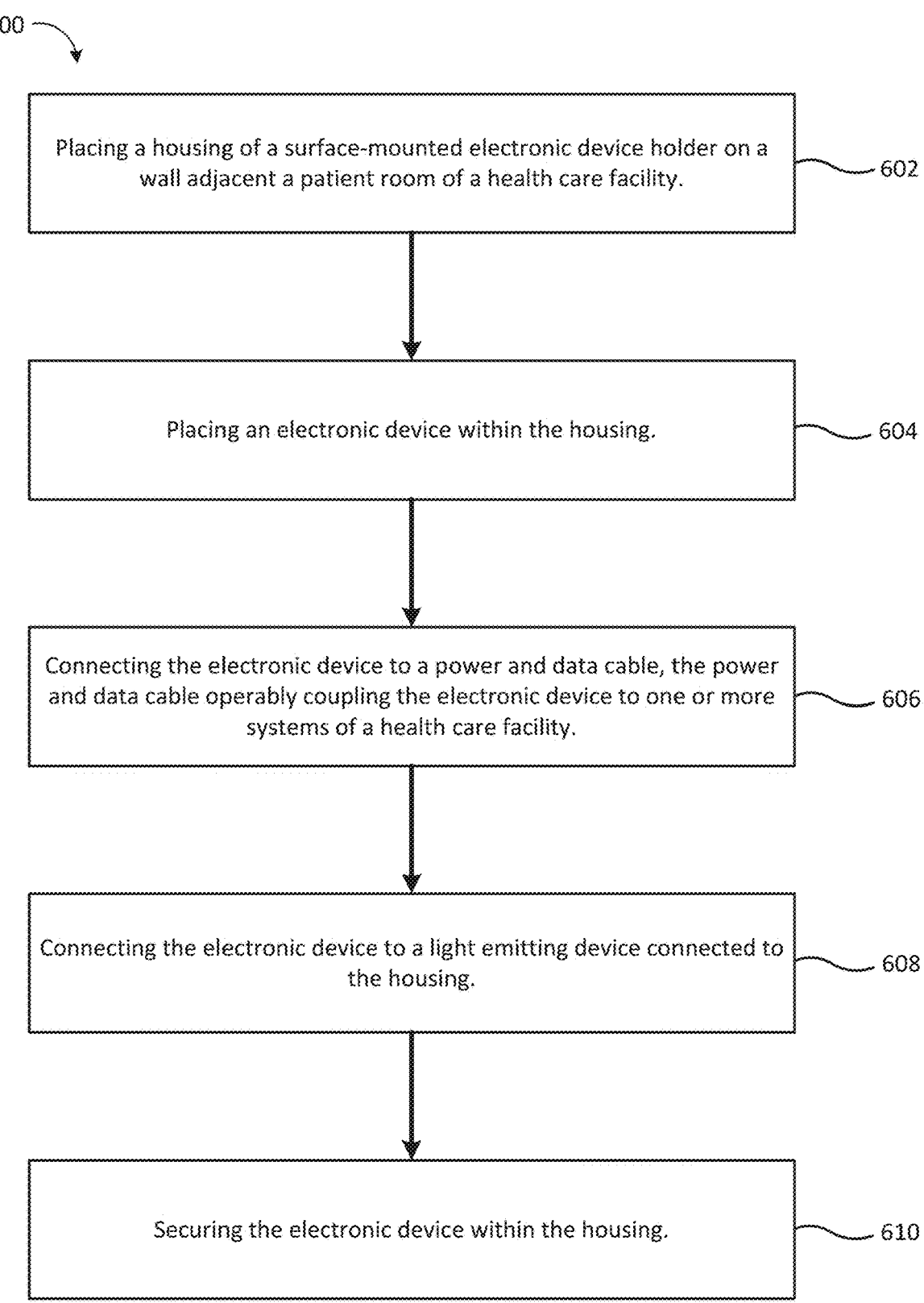
FIG. 6 is a simplified schematic diagram of a method of installing the surface-mounted PED holder assembly, in accordance with some embodiments.

FIG. 6 is a simplified schematic diagram of a method 600 of installing the wall-mounted PED holder assembly, in accordance with some embodiments. The wall-mounted PED holder assembly may be the surface-mounted PED holder 104 in some examples. In some examples, the holder may be installed on a wall or surface of a hospital or health care facility, for example adjacent an entry to patient room, in a hallway, within a patient room, adjacent a chair or bed, adjacent an exam table, or in any other suitable location.

At 602, the method 600 includes placing a housing of a surface-mounted electronic device holder on a wall adjacent a patient room of a health care facility. The housing may include a mounting plate, such as back 116B of FIG. 5. The back 116B may be secured to the wall using any suitable attachment means for securing to a wall or surface in a permanent or non-permanent manner.

At 604, the method 600 includes placing an electronic device within the housing. The electronic device may be a self-contained device such as a computer or tablet or may be a series of components connected or operably coupled together, such as a processor, memory, display device, and other such components. The electronic device may be placed within the housing such that the display is visible through an opening in the housing. The electronic device may be supported by supports to resist movement of the electronic device within the housing once installed.

At 606, the method 600 includes connecting the electronic device to a power and data cable, the power and data cable operably coupling the electronic device to one or more systems of a health care facility. The power and data cable may be connected to an interface as described herein, including a POE connection or other such connection to provide power and/or data connection to the electronic device.

At 608, the method 600 includes connecting the electronic device to a light emitting device connected to the housing. The electronic device may power the light emitting device or the light emitting device may include a separate power source. The light emitting device may include color-configurable light elements, projectors, such as to project an image, incandescent lights, LEDs, fluorescent lights, and the like. The electronic device may also be connected to other devices including, for example a handwashing station, a flag or visual marker, or any other suitable device that may be connected to the electronic device. Additional devices may include communication devices, proximity sensors, authentication devices, RFID sensors, Near Field Communication (NFC) devices, Bluetooth devices, biometric devices, wireless communication devices, and/or the like. In some examples, the flag or other such movable features may be actuated in response to a signal from the electronic device or a health care system. The flag or other such movable feature may be connected to a motor, such as a stepper motor, and the signal may cause the motor or any other suitable actuator to change a position of the flag, for example to draw attention to a room, indicate occupancy of a room, or provide other such signals as visual cues.

At 610, the method 600 includes securing the electronic device within the housing. The housing may be closed around the electronic device by securing portions of the housing together to enclose the electronic device. In some examples the housing may include a removable access panel that may be secured. The electronic device may be secured with security devices such as security screws, magnetic latches, sliding locks, and other such devices.

Figure 7:
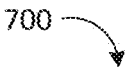
FIG. 7 is a simplified schematic diagram of a method of authenticating a user identity to display additional data at a wall-mounted electronic device within a PED holder assembly, in accordance with some embodiments.
Figure 7:
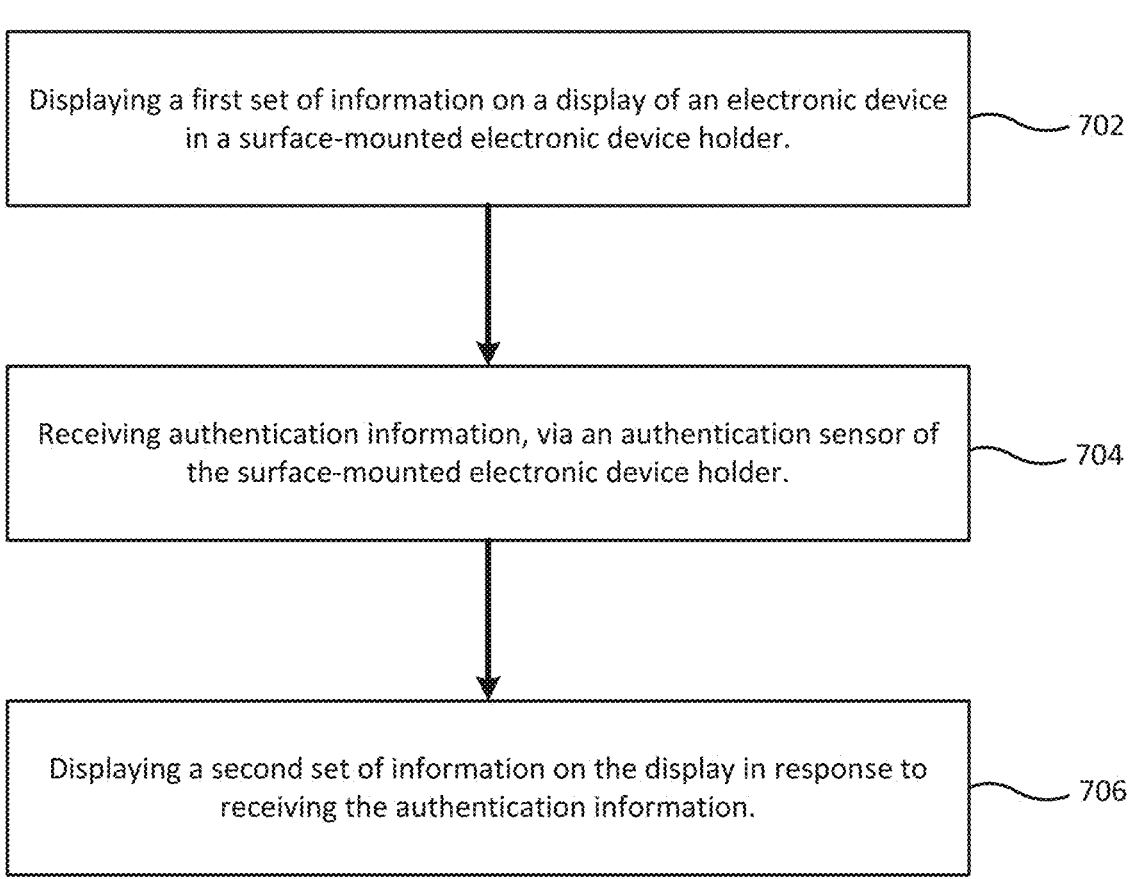

FIG. 7 is a simplified schematic diagram of a method 700 of authenticating a user identity to display additional data at a wall-mounted electronic device within a PED holder assembly, in accordance with some embodiments.

At 702, the method 700 includes displaying a first set of information on a display of an electronic device in a surface-mounted electronic device holder. The first set of information may include generic information about a room or facility. The generic information may not include any personalized or secure information. The first information may be received from a remote device accessed over a wired connection to the electronic device. The electronic device in the surface-mounted electronic device holder may, for example, be positioned outside a patient room in a health-care facility. Initially only information that is not privacy-protected may be displayed or visible on the screen. The information may be read-only such that no information may be editable or added prior to authentication.

At 704, the method 700 includes receiving authentication information, via an authentication sensor of the surface-mounted electronic device holder. The authentication sensor may include a proximity sensor, an RFID sensor, Near Field Communication (NFC) devices, Bluetooth devices, a biometric sensor, and/or other such devices to detect and verify an identify of an individual in proximity of the surface-mounted device holder. The electronic device may, for example receive a signal from a proximity sensor indicating an individual in proximity of the holder. In response, the electronic device may display a request for credentials or may activate one or more authentication devices for receiving authentication data. The electronic device may receive the credentials through the authentication device.

At 706, the method 700 includes displaying a second set of information on the display in response to receiving the authentication information. The second set of information may be displayed only after an identity of the individual is authenticated as in step 704. The second set of information may include healthcare data, such as a patient electronic health record or treatment records. Other such private information may be included in the second set of information. The second set of information may be read/write accessible such that an authenticated individual may add or revise information, for example to update a patient health or treatment log after visiting the patient. In some examples additional actions may be triggered by the electronic device after authenticating at 704. For example, a prompt may be displayed to wash or sanitize hands before entering the room, with a hand sanitizer connected to the electronic device capable of confirming use before allowing access into the room or before indicating, on the display, it is safe to proceed into the room. Additional data may be downloaded or uploaded to or from an individual's electronic device, such as a tablet of a treating physician to update a patient log in a hospital database following treatment of the patient.

Figure 8:
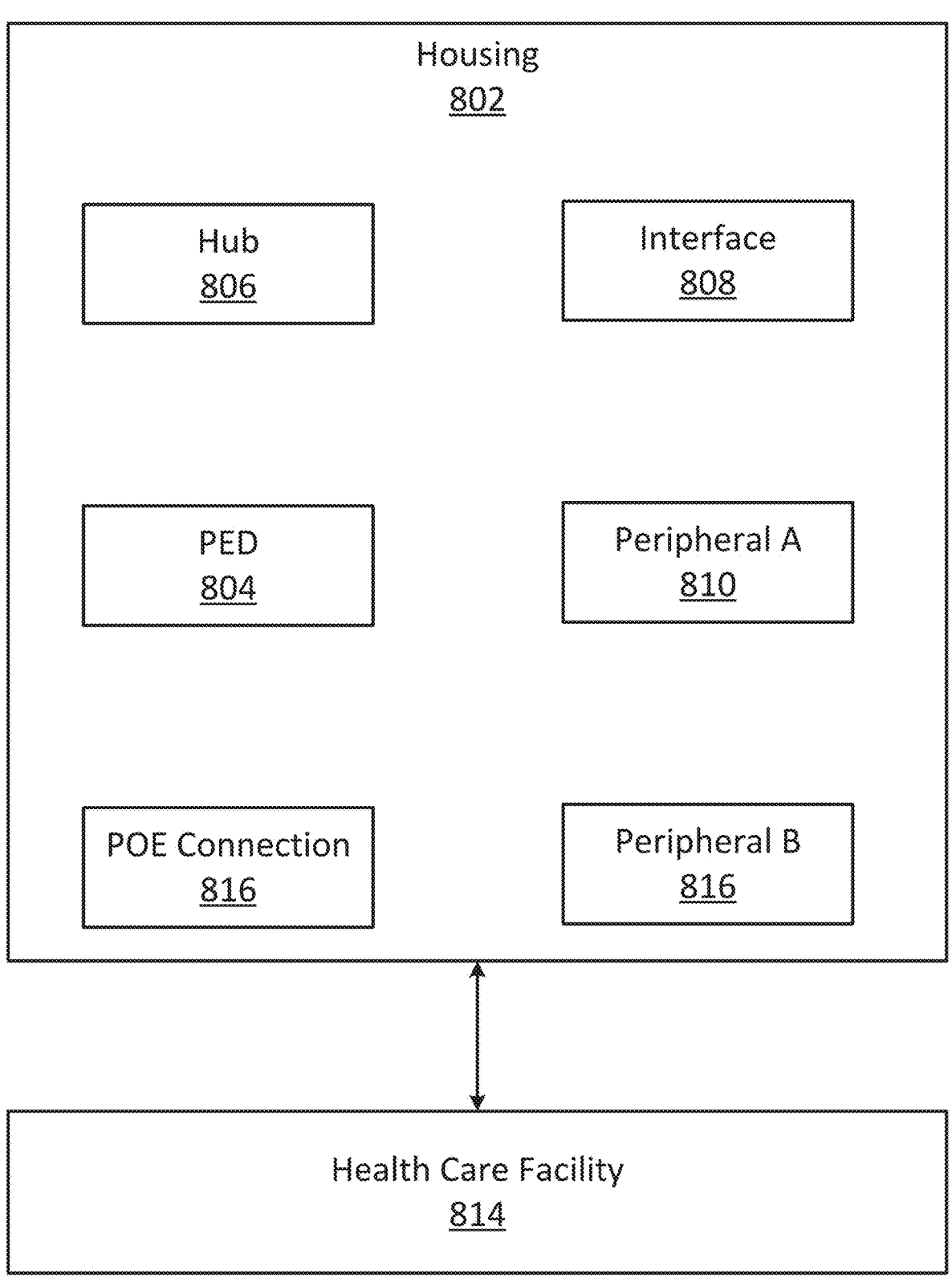
FIG. 8 is a simplified block diagram of elements included in a PED holder assembly and connections between system elements, in accordance with some embodiments.

FIG. 8 is a simplified block diagram of a system 800 of a PED holder assembly and connections between system elements, in accordance with some embodiments. The system includes a housing 802, a PED 804, a hub 806, an interface 808, a peripheral A 810, a peripheral B 812, a POE connection 816, and a health care facility system 814. The housing 802 may be the same as PED holder 14 or surface-mounted electronic device holder 104 described above, including any variations thereof. The housing 802 may connect to a surface of a health care facility, a rail of a bed in a health care facility, or any other rail or surface. The PED 804 is likewise similar to the PED described herein and may include a self-contained computing device and/or a custom-built computing device contained within the housing 802. The peripherals 810 and 812 may include additional devices such as lighting elements, projectors, authentication sensors, proximity sensors, communication devices, displays, screens, touch screens, disinfecting units (e.g., including UV lights, dispensing units, anti-microbial cleaning units, etc.), RTLS devices, NFC devices, RFID devices, device chargers, built-in display (e.g., for screen mirroring/extending), a negative pressure control screen, and other such additional components combined within the housing 802.

In various embodiments, the surface-mounted electronic device holder 104 can include hardware for interfacing with one or more of the peripherals. For example, the surface-mounted electronic device holder 104 can include hardware connections to connect with one or more of the peripheral systems.

The housing 802 and the PED 804 may include or be connected to various systems and other elements as described herein, including the health care facility system 814, an interface 808, peripheral A 810, and peripheral B 812. The POE connection 816 may optionally provide power to the hub 806, the interface 808, the PED 804, and optionally to the peripherals 810 and 812 or other devices connected to the housing 802. The POE connection may provide data and power connections between the housing 802 and the health care facility 814. The elements within the housing 802 may be connected through wired connections, or may be connected through wireless, BLUETOOTH®, or any other communication means or technology. Additionally, the housing 802 may be able to perform all required calculations or logic and perform all methods internally, i.e., without connection to an external server. In some examples an external server, such as the health care facility system 814 may be in communication with the elements within the housing 802, over wired or wireless connections, such as POE connections as described herein, however the health care facility system 814 may not be performing the steps of the methods or any required actions. In some examples, the external server may perform some portion of the methods described herein.

The hub 806 may include connections to the various other elements within the housing 802 and may perform intermediate conveyance of instructions and data between different elements of the system. For example, the hub 806 may be connected to the PED 804 and the peripherals 810 and 812 through wired or wireless connections. The hub 806 may include a processor and memory and be capable of receiving instructions or data from the PED 804, the health care facility system 814, interface 808, or the peripherals 810 and 812 and communicating the data, or some portion of the data to any other system element. In an example, the PED 804 may send instructions to illuminate an illumination element, which may be peripheral A 810. The illumination element may include lights or projectors to illuminate an environment surrounding the housing 802 and may not, for example, include backlit elements for buttons or other such illumination devices. The hub 806 may receive the instructions from the PED 804 and may communicate with a driver of the illumination element to illuminate the lighting element in the instructed manner. In such examples, the hub may include wired connections to a driver board or circuit for the peripheral, or may include the driver elements for the peripherals as components of the hub 806. In various embodiments, the hub 806 may be or include a processor. The 806 may be used to communicate with the various other elements within the housing 802 and may additionally or alternatively be used to communicate with elements outside of the housing 802. For example, the hub 806 may be used to communicate with devices positioned in the patients room 100.

In some examples, the hub 806 can be used to communicate with other surface-mounted electronic device holders 104. For example, the hub 806 can be used as part of a mesh network to communicate with other surface-mounted electronic device holders 104 and/or other electronic devices (e.g., devices containing NFC communication, Bluetooth communication, RFID communication). Additionally or alternatively, the hub 806 can be coupled to one or more communication devices of the surface-mounted electronic device holder 104, where at least one of these devices is a member of the mesh network. Further, the hub 806 can provide pass-through power or converted power (e.g., step-up/step-down) power to one or more the communication devices and/or other peripherals.

In some examples, the interface 808 may include an assistance request button, such as the assistance request button 62 described above. The assistance request button may be actuated and cause a signal to be conveyed to the PED 804 through the hub 806. The hub may be capable of connecting to multiple devices such as the peripherals 810 and 812 in addition to the interface 808 while still only requiring a single connection to the PED 804, thereby enabling use of self-contained PED devices such as mobile devices and tablets.

The communications between the hub 806 and the PED 804 may be identified, e.g., to identify the source of a signal as from peripheral A 810 or interface 808 based on a pin identity associated with the hub 806. In some examples, data may be appended with an identity of a peripheral device associated with the data as it is manipulated and conveyed by the hub 806. In some examples, the PED 804 may act as a host device with the hub 806 acting as an agent of the PED 804.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A surface-mounted electronic device holder comprising:
a housing to contain an electronic device including a display or an authentication sensor that is at least partially unobstructed by the housing, the housing comprising a first portion adapted for mounting the surface-mounted electronic device holder to a surface of a health care facility, wherein the electronic device is releasably detachable from the housing and carriable for a range;
a light source that is included in the housing, is different from the display, and is configured to receive health care-related instructions from at least one of: (i) the electronic device, (ii) a second electronic device, or (iii) a communication system of the health care facility, and output light based on the health care-related instructions; and
a set of interfaces disposed in the housing, wherein:
a first interface of the set of interfaces is operatively coupleable with the electronic device such that at least one of power or data is passed between the first interface to the electronic device, or
a second interface of the set of interfaces is operatively coupled with the communication system of the health care facility such that a signal is passed between the second interface and the communication system.

2. The surface-mounted electronic device holder of claim 1, wherein the light source comprises one or more color-configurable lights positioned around a perimeter of the housing.

3. The surface-mounted electronic device holder of claim 2, wherein the color-configurable lights provide an indication of at least one of: (i) a room status of a room in the health care facility or (ii) a patient status of a patient of the health care facility; and
wherein the color-configurable lights display at least one color with controllable brightness based on the health care-related instructions.

4. The surface-mounted electronic device holder of claim 1, wherein the light source projects graphical information on a wall, a door, a ceiling, or a floor of the health care facility.

5. The surface-mounted electronic device holder of claim 4, wherein the light source provides an indication of at least one of: (i) a room status of a room in the health care facility or (ii) a patient status of a patient of the health care facility.

6. The surface-mounted electronic device holder of claim 4, wherein the graphical information comprises an image, the image displayed based on the health care-related instructions and showing at least one of: (i) a room status of a room in the health care facility, (ii) a patient status of a patient of the health care facility, or (iii) directions for health care personnel.

7. The surface-mounted electronic device holder of claim 1, wherein light emitted by the light source changes in at least one of (i) color or (ii) brightness in response to an indication of an action being performed.

8. The surface-mounted electronic device holder of claim 1, wherein the set of interfaces includes at least one interface adapted for connection to a cable of the health care facility for at least one of power or data.

9. The surface-mounted electronic device holder of claim 1, wherein the housing further comprises internal cradling configured to support the electronic device and align the display of the electronic device with an opening.

10. A surface-mounted electronic system for placement outside a patient room, the surface-mounted electronic system comprising:
a first housing enclosing an interior volume;
a second housing comprising a first display or authentication sensor, wherein the second housing is releasably detachable from the first housing and carriable for a range;
the first display or the authentication sensor at least partially unobstructed by the first housing;
a processor coupled with the first display, the processor configured to send and receive data associated with the surface-mounted electronic system;
a first interface coupled with the first display or the authentication sensor such that power received from a power cable is provided from the first interface to the first display or the authentication sensor; and
a light source that is included in the first housing, is different from the first display, and is configured to receive health care-related instructions from at least one of: (i) the processor, (ii) a second electronic device, or (iii) a communication system of a health care facility, and output light based on the health care-related instructions.

11. The surface-mounted electronic system of claim 10, wherein the first housing further defines a slot for receiving a portable electronic device.

12. The surface-mounted electronic system of claim 11, wherein the slot comprises a charging device coupleable with the portable electronic device when the portable electronic device is positioned within the slot.

13. The surface-mounted electronic system of claim 11, further comprising an ultraviolet light emitter.

14. The surface-mounted electronic system of claim 10, further comprising a camera for capturing image data of an individual outside the patient room.

15. The surface-mounted electronic system of claim 10, wherein the light source selectively illuminates based on a signal from the processor indicating a first condition within the patient room or a second condition outside of the patient room.

16. The surface-mounted electronic system of claim 10, wherein the communication system includes a network.

17. The surface-mounted electronic system of claim 10, further comprising a second display coupled with the processor.

18. A method, comprising:
placing a housing of a surface-mounted electronic device holder on a surface adjacent a patient room of a health care facility;
connecting an electronic device to the housing, wherein the electronic device includes a display or an authentication sensor, wherein the electronic device is releasably detachable from the housing and carriable for a range;
coupling the electronic device to one or more systems of the health care facility;
connecting the electronic device to a light source connected to the housing, wherein the light source is different from the display and is configured to receive health care-related instructions from at least the electronic device and output light based on the health care-related instructions; and
securing the electronic device within the housing.

19. The method of claim 18, wherein the housing comprises a first portion and a second portion, the first portion and the second portion enclosing a space to contain the electronic device including the display and the first portion defining an opening through which the display is accessible by a user, and one or more interfaces adapted for connection to the one or more systems of the health care facility, the one or more interfaces disposed in the housing.

20. The method of claim 18, further comprising connecting the electronic device to a sensor, the sensor configured to detect information relating to an individual outside the patient room and convey the information to the electronic device for selectively presenting patient information on the display of the electronic device in response to receiving the information.

* * * * *